(12) United States Patent
Allen

(10) Patent No.: US 7,169,117 B2
(45) Date of Patent: Jan. 30, 2007

(54) INTEGRATED LANCE AND STRIP FOR ANALYTE MEASUREMENT

(75) Inventor: John J. Allen, Mendota Heights, MN (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 11/231,130

(22) Filed: Sep. 20, 2005

(65) Prior Publication Data

US 2006/0074351 A1    Apr. 6, 2006

Related U.S. Application Data

(63) Continuation of application No. 10/460,030, filed on Jun. 11, 2003, now abandoned.

(60) Provisional application No. 60/458,242, filed on Mar. 28, 2003.

(51) Int. Cl.
*A61B 5/00* (2006.01)
*B65D 81/00* (2006.01)

(52) U.S. Cl. .................................................. 600/584

(58) Field of Classification Search ................ 600/309, 600/365, 368, 573, 576, 583, 584; 606/181–183; 422/50, 55, 100; 435/4, 14; 204/403.01; 73/864.01, 864.02
See application file for complete search history.

(56) References Cited

U.S. PATENT DOCUMENTS

| | | | |
|---|---|---|---|
| 59,306 A | 10/1866 | Wolff | |
| 3,303,959 A | 4/1962 | Grunert | |
| 3,143,793 A | 8/1964 | Griffiths et al. | |
| 3,626,929 A | 12/1971 | Sanz et al. | |
| 3,741,197 A | 6/1973 | Sanz et al. | |
| 3,831,814 A | 8/1974 | Butler | |
| 4,585,446 A | 4/1986 | Kempf | |
| 4,713,165 A | 12/1987 | Conover et al. | |
| 4,753,641 A | 6/1988 | Vaslow | |
| 4,873,993 A | 10/1989 | Meserol et al. | |
| 4,924,879 A | 5/1990 | O'Brien | |
| 5,669,543 A | 9/1997 | Ueno | |
| 5,700,695 A | 12/1997 | Yassinzadeh et al. | |
| 5,708,247 A | 1/1998 | McAleer et al. | |
| 5,820,570 A * | 10/1998 | Erickson et al. ............. | 600/573 |
| 5,855,801 A | 1/1999 | Lin et al. | |
| 5,857,983 A * | 1/1999 | Douglas et al. ............. | 600/583 |
| 5,928,207 A * | 7/1999 | Pisano et al. ................ | 604/272 |

(Continued)

FOREIGN PATENT DOCUMENTS

EP        0352138 A2    1/1990

(Continued)

OTHER PUBLICATIONS

Somnoplasty Palate Handpiece "A Simple Treatment for Habitual Snoring", Gyrus ENT, Bartlett, TN 38133, US, 2001 Somnus Medical Technologies, Inc., 1010-2110-05.

*Primary Examiner*—Max F. Hindenburg
*Assistant Examiner*—Brian Szmal

(57) ABSTRACT

The present invention relates, in general, to lancing elements for use in drawing bodily fluids out of a patient and, more particularly, to an improved lancing element including first and second elements positioned relative to each other such that an incision formed by the first element is held open by the second element and bodily fluids are pulled up the lancing element by surface tension on the first and second lancing elements.

7 Claims, 3 Drawing Sheets

U.S. PATENT DOCUMENTS

| | | |
|---|---|---|
| 5,938,679 A | 8/1999 | Freeman et al. |
| 5,951,836 A | 9/1999 | McAleer et al. |
| 5,989,917 A | 11/1999 | McAleer et al. |
| 6,015,392 A | 1/2000 | Douglas et al. |
| 6,046,051 A | 4/2000 | Jina |
| 6,086,545 A | 7/2000 | Roe et al. |
| 6,139,562 A | 10/2000 | Mauze et al. |
| 6,153,085 A | 11/2000 | Patko et al. |
| 6,173,202 B1 | 1/2001 | Eppstein |
| 6,193,873 B1 | 2/2001 | Ohara et al. |
| 6,241,862 B1 | 6/2001 | McAleer et al. |
| 6,284,125 B1 | 9/2001 | Hodges et al. |
| 6,332,871 B1 | 12/2001 | Douglas et al. |
| 6,364,890 B1 | 4/2002 | Lum et al. |
| 6,444,115 B1 | 9/2002 | Hodges et al. |
| 6,475,372 B1 | 11/2002 | Ohara et al. |
| 6,544,475 B1 | 4/2003 | Douglas et al. |
| 6,558,528 B1 | 5/2003 | Matzinger |
| 6,591,124 B2 | 7/2003 | Sherman et al. |
| 6,607,658 B1 | 8/2003 | Heller et al. |
| 6,612,111 B1 * | 9/2003 | Hodges et al. .............. 60/583 |
| 6,620,310 B1 | 9/2003 | Ohara et al. |
| 6,706,159 B2 | 3/2004 | Moerman et al. |
| 6,716,577 B1 | 4/2004 | Yu et al. |
| 6,793,633 B2 | 9/2004 | Douglas et al. |
| 2001/0056284 A1 | 5/2001 | Purcell et al. |
| 2002/0082522 A1 | 6/2002 | Douglas et al. |
| 2002/0168290 A1 * | 11/2002 | Yuzhakov et al. ............ 422/56 |
| 2002/0177788 A1 | 11/2002 | Hodges |
| 2003/0018282 A1 | 1/2003 | Effenhauser et al. |
| 2003/0083686 A1 | 5/2003 | Freeman et al. |
| 2003/0143113 A2 * | 7/2003 | Yuzhakov et al. ............ 422/56 |
| 2003/0171699 A1 * | 9/2003 | Brenneman ................. 600/584 |
| 2004/0096959 A1 | 5/2004 | Stiene et al. |
| 2004/0106941 A1 * | 6/2004 | Roe et al. .................... 606/181 |

FOREIGN PATENT DOCUMENTS

| | | |
|---|---|---|
| EP | 1112717 A1 | 7/2001 |
| GB | 2374019 | 10/2002 |
| WO | WO 95/10221 A | 4/1995 |
| WO | WO 97/19344 A | 5/1997 |
| WO | WO 00/22977 A | 4/2000 |
| WO | WO 01/64105 A | 9/2001 |
| WO | WO 01/67099 A1 | 9/2001 |
| WO | WO 01/72220 A1 | 10/2001 |
| WO | WO 01/73109 A2 | 10/2001 |
| WO | WO 01/73124 A2 | 10/2001 |
| WO | WO 02/06806 A2 | 1/2002 |
| WO | WO 02/024322 A3 | 3/2002 |
| WO | WO 02/49507 A1 | 6/2002 |
| WO | WO 02/50534 A1 | 6/2002 |
| WO | WO 02/100461 A2 | 12/2002 |
| WO | WO 04/41087 A | 5/2004 |
| WO | WO 04/041087 A2 | 5/2004 |

* cited by examiner

INTEGRATED LANCE AND STRIP FOR ANALYTE MEASUREMENT

CROSS-REFERENCE

This is a continuation application of U.S. application Ser. No. 10/460,030 filed Jun. 11, 2003, now abandoned which is incorporated herein by reference. This application claims priority to Provisional Application No. 60/458,242 filed Mar. 28, 2003, which is incorporated herein by reference in its entirety.

BACKGROUND OF THE INVENTION

1. Field of the Invention

The present invention relates, in general, to lancing elements for use in drawing bodily fluids out of a patient and, more particularly, to an improved lancing element including first and second elements positioned relative to each other such that an incision formed by the first element is held open by the second element and bodily fluids are pulled up the lancing element by surface tension on the first and second lancing elements.

2. Description of the Related Art

Integrated skin lancing and body fluid analysis samplers are known in the art. One such system is described and illustrated in WO 02/49507. The integrated system described in WO 02/49507 includes a lancing element or lance, which is attached to or integrated with a test strip adapted to measure the quantity of an analyte in bodily fluid or, alternatively, some characteristic of the bodily fluid. Usable bodily fluids may include, for example, blood or interstitial fluid (ISF). The lancing element is used to make an incision in the skin and the bodily fluid is drawn up the lancing element to the test strip by, for example, capillary action. Such integrated samplers may be combined with, for example, an electrochemical meter and referred to as monolithic or in-situ sampling devices.

Many lancing devices have been devised to form incisions and to enable bodily fluids to be withdrawn from those incisions. Solid lancets are used to open an incision in the skin to allow bodily fluids to escape to the surface of the skin where they can be sampled by the patient or the doctor. In order to ensure that enough fluid is released from the incision, such solid lancing elements are generally larger in diameter to facilitate the flow of sufficient bodily fluids from the incision for sampling purposes. However, such solid needles generally rely on the size of the incision to ensure that enough bodily fluids are expressed and are not used to facilitate the flow of fluids to the testing apparatus.

Hollow needles have also been described for use in drawing fluids out of the body for testing purposes; such needles may have a pointed or beveled end to facilitate opening the incision. In such needles, the incision is held open by the outer diameter of the needle to facilitate the flow of bodily fluids out of the incision and the bodily fluids are drawn up the needle either by a vacuum or by capillary action or by a combination of vacuum and capillary action.

Other lancing devices have been described wherein the lance is a flat or partially curved piece which includes an open channel for guiding fluid from the sharpened tip to the proximal end of the lance by means of, for example, surface tension and/or capillary action. Such lancing elements are advantageous because of the ease of manufacture and the ease of integrating them into, for example, a test strip, in order to facilitate both lancing and measurement in a single element. Where the landing element is a flat or partially flat piece which includes an open channel for guiding fluid, it is possible for the edges of the incision to close on the channel, fully or partially blocking the channel and preventing bodily fluids from flow to the proximal end of the channel or limiting the amount of fluid which can flow.

Problem to be Solved

It would, therefore, be advantageous to design a lancing device where the lancing element is a flat or partially curved piece including an open channel and the lancing element includes a separation element for holding the incision open when the lancing element is in the wound and preventing the edges of the incision from closing on the lancing element and partially or fully blocking the open channel. It would be advantageous to design a lancing device wherein the separation element is positioned slightly proximal to the sharpened tip of the lancing element to facilitate insertion of the lance into the skin. It would further be advantageous to design a lancing device wherein the lancing element and the separation element are formed from a single metal sheet. It would further be advantageous to design a lancing device wherein the lancing element and the separation element are positioned opposite each other such that fluid is pulled up the lancing element and into the open channel by surface tension between the fluid and the lancing element and separation element, thus facilitating the filling of the channel. It would further be advantageous to design a lancing device wherein the lancing element and the separation element are formed from a single sheet of metal rolled to position the separation element opposite the lancing element such that the proximal end of the lancing element and the separation element form an open channel. It would further be advantageous to manufacture the lancing devices described herein using, for example, a metal forming or stamping process.

SUMMARY OF THE INVENTION

A lance according to the present invention includes a lancing element having a first sharpened end point, a separation element having a second sharpened end point wherein the second sharpened end point is positioned proximal to the first sharpened end point, a connector connecting a proximal portion of the first lancing element to a proximal portion of the separation element, the connector forming a channel. In a further embodiment of the present invention, the separation element is positioned at an angle to the lancing element. In a further embodiment of the present invention the lancing element, the separation element and the channel are formed from a single sheet of metal. In a further embodiment of the present invention, a space between the lancing element and the separation element forms a gap, the gap increasing in size proximal to the second sharpened tip. In a further embodiment of the present invention, least a portion of the channel is treated with a hydrophilic surface coating. In a further embodiment of the present invention, at least a portion of the lancing element and at least a portion of the separation element are coated with a hydrophilic surface coating. In a further embodiment of the present invention, a proximal end of the channel is integrated into a sensor strip. In a further embodiment of the present invention, the sensor strip is connected at a proximal end thereof to a plurality of additional sensor strips

BRIEF DESCRIPTION OF THE DRAWINGS

While the novel features of the invention are set forth with particularity in the appended claims, a better understanding of the features and advantages of the present invention will be obtained by reference to the following detailed description that sets forth illustrative embodiments, in which the principles of the invention are utilized, and the accompanying drawings of which:

DETAILED DESCRIPTION OF ILLUSTRATIVE EMBODIMENTS OF THE INVENTION

Figure 1:
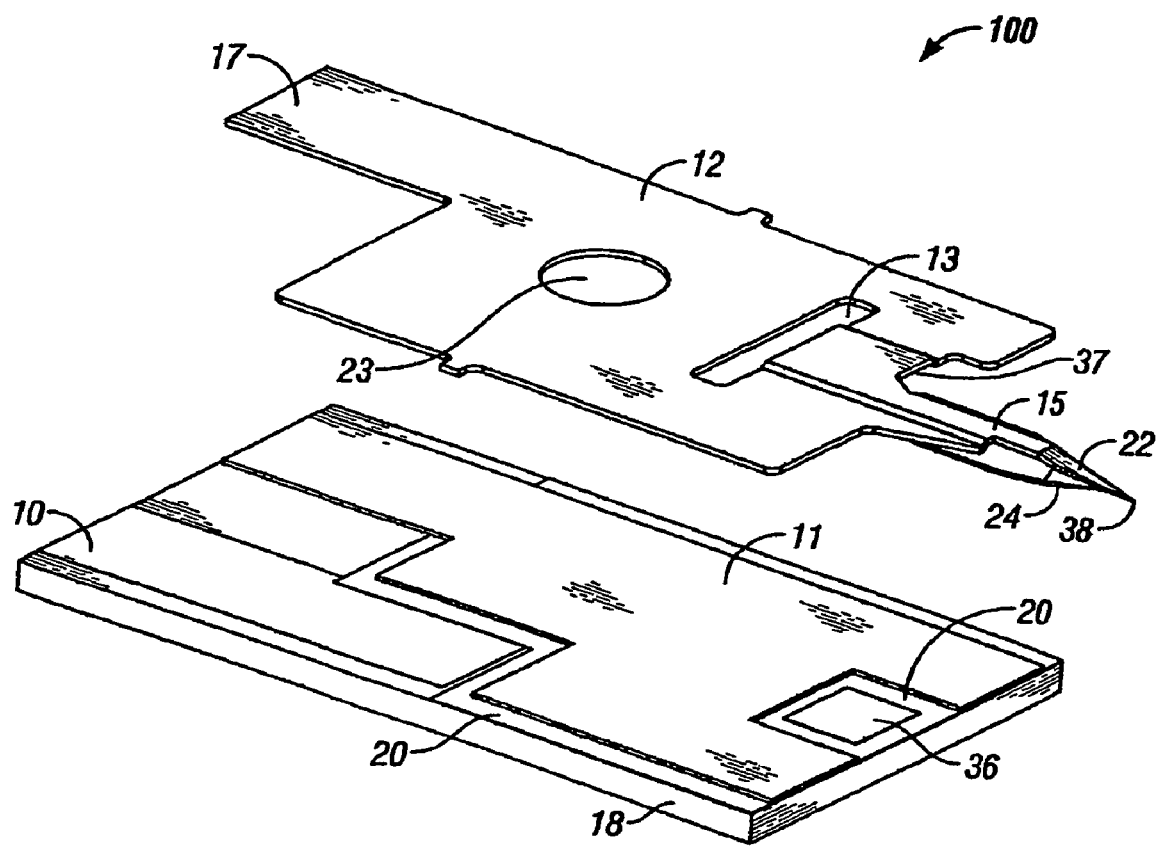
FIG. 1 is a perspective view of a lancing element and strip according to the present invention.

FIG. 1 is a perspective view of lance 15 and sensor strip 100 according to the present invention. In FIG. 1, lance 15 is connected to sensor strip 100. Sensor strip 100 may be, for example, a glucose sensor strip which uses electrochemistry to measure the amount of glucose in a bodily fluid, such as, for example, blood or interstitial fluid. Additionally, sensor strip 100 may be, for example, a coagulation sensor which measures a physical characteristic of a body fluid such as viscosity, capacitance, resistance, and the like. In FIG. 1, lance 15 further includes lancing element 22 and separation element 24. Sensor strip 100 further includes first electrode contact 10, adhesive layer 11, conductive substrate 12, vent hole 13, second electrode contact 17, insulating substrate 18, insulating layer 20, registration hole 23 and working electrode 36. In an embodiment of the invention, sensor strip 100 may have an approximate width of 0.22 inches and an approximate length of 0.55 inches.

Figure 2:
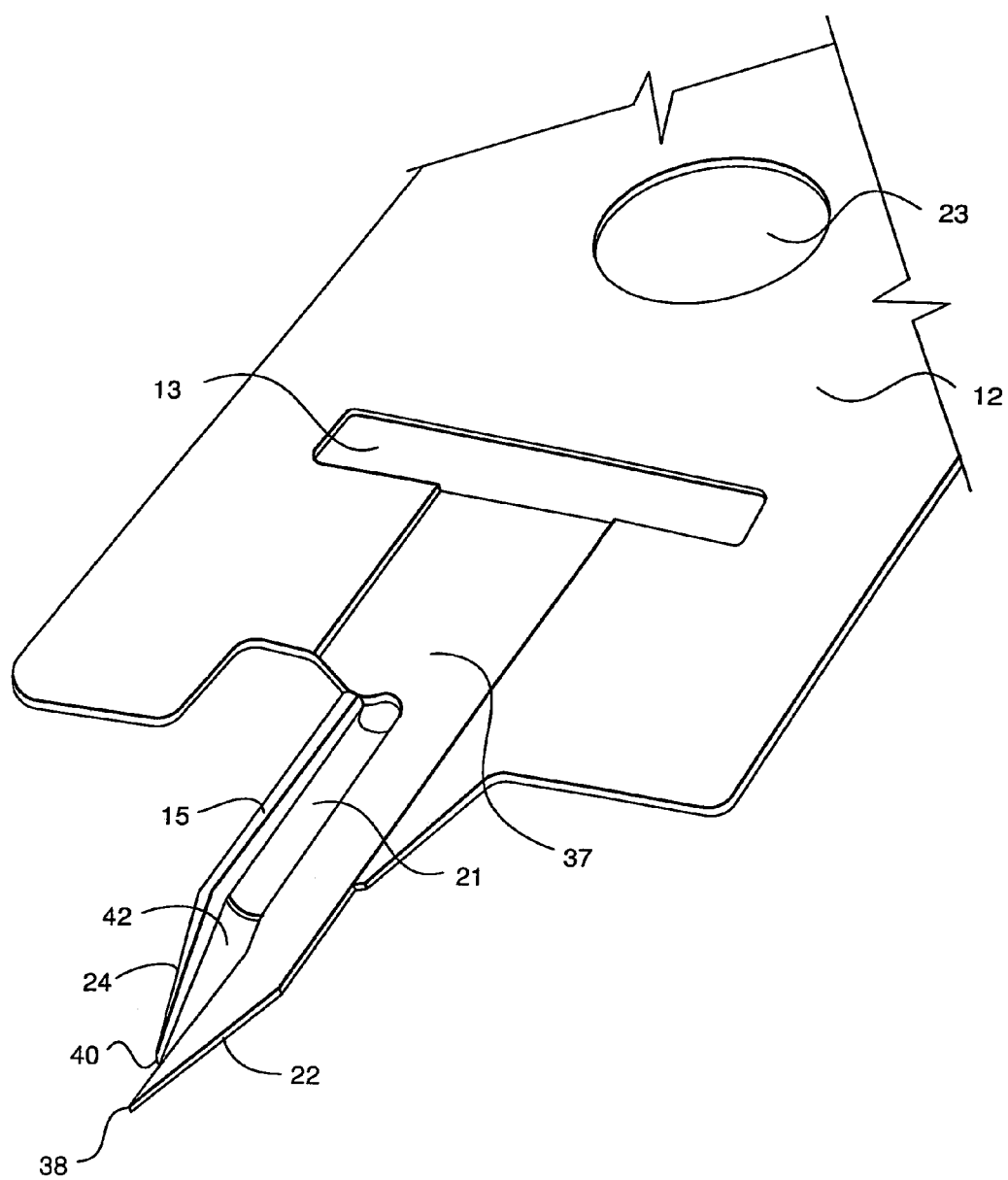
FIG. 2 is a perspective view of the top layer of a lancing element and strip according to the present invention.

FIG. 2 is a perspective view of lance 15 and the top layer of sensor strip 100 for use in the present invention. In FIG. 2, the top layer of sensor strip 100 and lance 15 is formed from conductive substrate 12. In the embodiment illustrated in FIG. 2, conductive substrate 12 includes vent hole 13 and registration hole 23. In FIG. 2, lance 15 includes lancing element 22, separation element 24 and fill channel 21.

One embodiment of a lancing element and sensor strip suitable for use in the present invention may be described with reference to FIGS. 1 and 2. In the embodiment illustrated in FIGS. 1 and 2, sensor strip 100 includes first electrode contact 10, wherein first electrode contact 10 may be screen printed on an insulating substrate 18, and a second electrode contact 17, wherein second electrode contact 17 comprises a portion of conductive substrate 12 which is contiguous with reference electrode 37 and lance 15. In the embodiment of the lancing element and sensor strip illustrated in FIGS. 1 and 2, the orientation of first electrode contact 10 and second electrode contact 17 are arranged such that an analyte measurement meter, such as, for example, a glucose meter (not shown) can establish electrical contact with sensor strip 100. In the illustrated embodiment, first electrode contact 10 and second electrode contact 17 are arranged on the same side of insulating substrate 18 to facilitate contact of both electrodes at the distal end of sensor strip 100.

Sensor strip 100 is manufactured using adhesive layer 11 to attach insulating substrate 18 to conductive substrate 12. Adhesive layer 11 could be implemented in a number of ways, including using pressure sensitive material, heat activated material, or UV cured double sided adhesive material. Conductive substrate 12 may be, for example, a sheet of electrically conductive material such as gold or plated stainless steel. The geometry of conductive substrate 12 may be formed by, for example, stamping process or photo etching. In the embodiment illustrated in FIGS. 1 and 2, lance 15 may be manufactured as an integral part of conductive substrate 12. Vent hole 13, may be formed by, for example, punching through conductive substrate 12. Vent hole 13 is used to facilitate the transport of bodily fluid up lance 15 and across working electrode 36. Registration hole 23 may be formed during the stamping process of making conductive substrate 12.

In one embodiment of the invention, an analyte sensing layer may be, for example, a glucose sensing layer, including an enzyme, a buffer, and a redox mediator. An analyte sensing layer (not shown) may preferably be deposited on top of working electrode 36. Where an analyte sensing layer is used to detect the presence and concentration of glucose in a bodily fluid, at least a portion of glucose sensing layer dissolves in the bodily fluid and is used to convert the glucose concentration into an electrically measured parameter which is proportional to the glucose concentration in the sample.

In the embodiment illustrated in FIGS. 1 and 2, lance 15 has a distal and proximal end and the proximal end is integrated with reference electrode 37 and the distal end includes sharpened tip 38 at the distal end of lancing element 22. Lance 15 may be formed by the process of stamping or photo-etching a conductive metal sheet. Photo-etching lance 15 is also beneficial in facilitating the manufacture of a lancing element which has a sharp lancing element 22 and separation element 24. In a subsequent process step, lance 15, lancing element 22, and separation element 24 may be bent to form a "V" or "U" shaped channel geometry as shown in FIG. 2. Fill channel 21 serves as a conduit from lancing element 22 and separation element 24 to working electrode 36 and reference electrode 37. In one embodiment of the present invention, the distal end of lacing element 22 and separation tip 40 of separation element 24 are offset by about 0.005 inches to 0.020 inches.

The design of lance 15 is adapted to more effectively cut skin due to a sharper leading point of lancing element 22. As illustrated in FIG. 2, with separation tip 40 offset distally from sharpened tip 38 of element 22, the extreme distal end of lance 15 comprises only sharpened tip 38 which may be a very sharp point or edge to facilitate the initial incision as lancing element 22 enters the skin. In contrast, if lancing element 22 and separation element 24 were coincident, the leading point of lance 15 would include both sharpened tip 38 and separation tip 40 making the combination less sharp than the embodiment illustrated in FIG. 2 and requiring more force to create the initial incision. The offset of sharpened tip 38 and separation tip 40 make lance 15 more manufacturable because it reduces the inherent alignment difficulties in bringing the sharp point of lancing element 22 and separation element 24 into alignment or contact with each other. The embodiment of the invention illustrated in FIGS. 1 and 2 is further beneficial because it enhances fluid egress by helping to spread and hold open the skin wound after the initial incision is made. In the embodiment illustrated in FIGS. 1 and 2, the lance 15 further includes reference electrode 37 and second electrode contact 17. Alternative embodiments may include forming all of the electrodes and electrode contacts on insulating substrate 18.

In the embodiment of the invention illustrated in FIG. 2, lance 15 includes fill channel 21, wherein the seamless transition between the lancing element 22 and separation element 24; and fill channel 21 facilitates the flow of body fluid from the wound to working electrode 36. Additionally, the seamless transition between the lancing element 22, separation element 24 and fill channel 21 prevents the introduction of stop junctions which can impede the capillary flow rate of liquid samples. The unique geometry increases the likelihood that a liquid sample will sufficiently cover working electrode 36 and reference electrode 37 regardless of the height of the lance 15 above or below the skin wound, or even if lance 15 lies horizontally offset from the wound. In certain embodiments of the invention, sample can be applied to the side of lance 15 rather than just the proximal end of lance 15 which provides a user the option of dosing sample onto sensor strip 100 after a site has been lanced separately.

In the embodiment of the invention illustrated in FIG. 2, the gap 42 between lancing element 22 and separation element 24 guides bodily fluids into fill channel 21. The increasing separation between lancing element 22 and separation element 24 as fluid moves distally towards fill channel 21 facilitates the drawing of fluid into fill channel 21 and from fill channel 21 to sensor strip 100. As gap 42 narrows towards a distal end of separation tip 40 of separation element 24, the surface tension between the bodily fluid in gap 42 and the walls of gap 42 increases, thus bodily fluid is drawn more readily into gap 42, and up into sensor strip 100. Gap 42 is also advantageous in that it facilitates the introduction of bodily fluids into fill channel 21 by facilitating the flow of bodily fluids positioned to the side of gap 42, thus enhancing the ways in which sensor strip 100 may be used to gather bodily fluids.

Fill channel 21 may facilitate the flow of bodily fluids by, for example, wicking or capillary action. In the embodiment illustrated in FIGS. 1 and 2, fill channel 21 has an open geometry which facilitates the wicking of viscous samples and provides for simpler manufacturing techniques when compared with closed capillary channels. For certain embodiments of the invention, fill channel 21 may be coated with a surfactant coating or undergo a hydrophilic surface treatment to increase the capillary force within fill channel 21. For certain embodiments of the invention separation element 24 and lancing element 22 may be coated with a surfactant coating or undergo hydrophilic surface treatment to increase the capillary flow force within gap 42. Additionally, the open geometry of fill channel 21 facilitates the wicking of sample because it prevents the formation of a vacuum block. In a closed channel geometry, a capillary inlet can become plugged if it is positioned too close to the wound or inside the wound preventing air from facilitating the flow of sample to the capillary. With the open geometry of fill channel 21, the proximal end of lance 15 can be positioned arbitrarily close to the source of the blood and allow for sufficient fill of sample. In this embodiment of the invention, the open geometry of fill channel 21 has the capacity to hold a larger sample volume than the minimum sample volume to cover reference electrode 37 and working electrode 36. The open geometry of fill channel 21 thus allows excess sample to accumulate along fill channel 21 which helps leave a cleaner wound site.

In the illustrated embodiment as shown in FIG. 2, the geometry of reference electrode 37 may be formed during the stamping process which effectively embosses the surface of conductive substrate 12. The stamping process may provide the pressure needed to create a recess in conductive substrate 12 which can help define the distance between reference electrode 37 and working electrode 36. For certain applications of the described invention, it may be advantageous to control the distance between reference electrode 37 and working electrode 36 by embossing conductive substrate 12 instead of controlling the thickness of adhesive layer 11. For other applications of the described invention, it may also be advantageous to not emboss the conductive substrate 12 and use adhesive layer 11 to help define the geometry of reference electrode 37.

In the embodiment of sensor strip 100 illustrated in FIG. 1, insulating substrate 18 consists of material such as polyester or ceramic on which a conductive material can be printed onto insulating substrate 18 through silk-screening, sputtering, or electro-less deposition. Conductive material deposited on insulating substrate 18 forms first electrode contact 10 and working electrode 36. Insulating layer 20 may be, for example, screen printed to form a boundary for first electrode contact 10 and working electrode 36.

Figure 3:
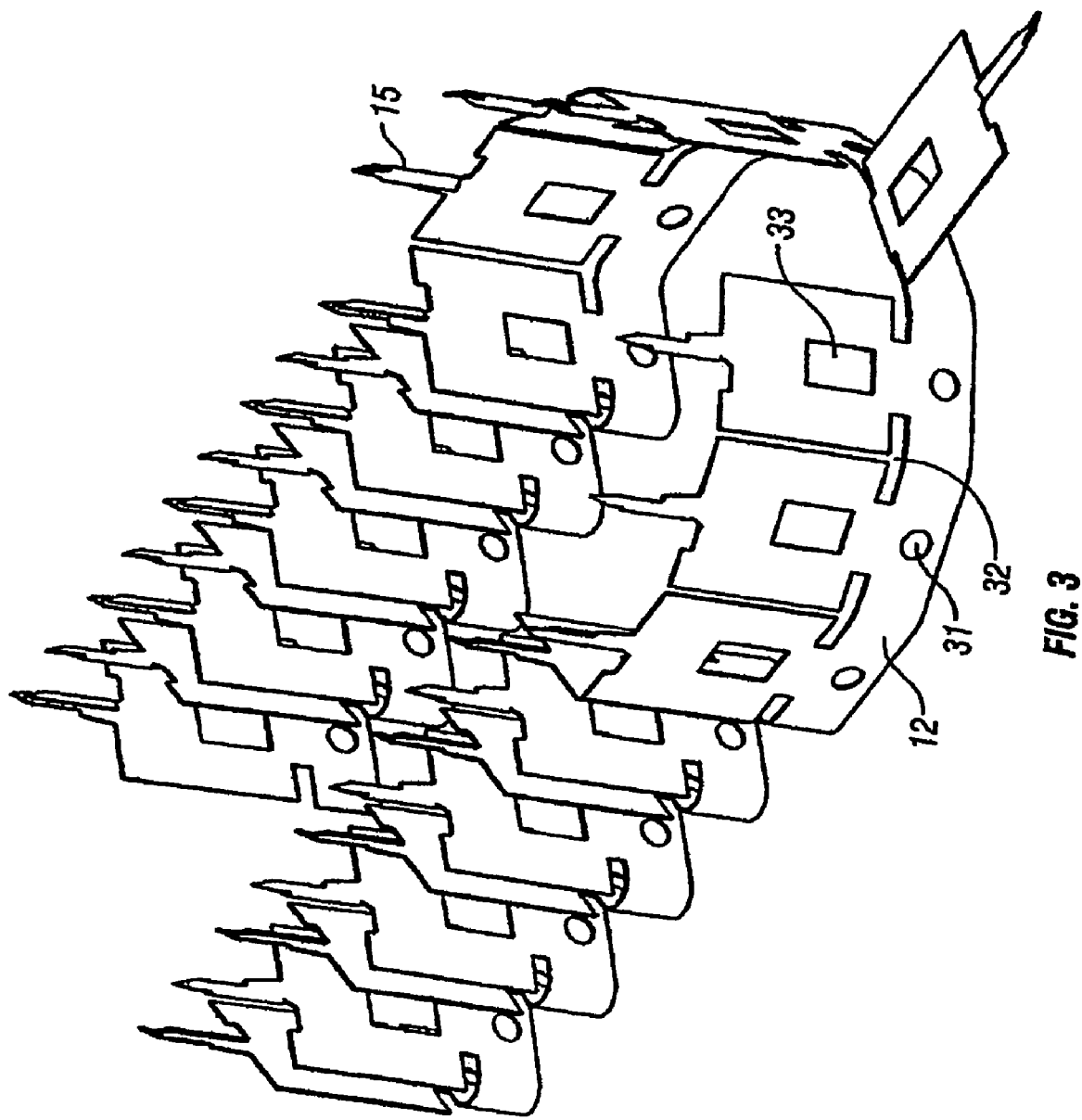
FIG. 3 is a perspective view of another embodiment of the invention in which multiple strips form an array of sensors for use in a cartridge format.

FIG. 3 is a perspective view of another embodiment of the invention in which multiple strips form an array of sensors for use in a cartridge format. Such an array may be inserted into a meter (not shown) having strips dispensed in a serial manner, one by one. The format of this embodiment allows a row of strips to be folded in a manner similar to an accordion wherein several strips similar to sensor strip 100 in FIG. 1 are attached together on an arrangement which facilitates their use in a cartridge. In FIG. 3, conductive substrate 12 is stamped in a progressive manner to form lance 15 such that several of them are chained together in series. The stamping process of conductive substrate 12 forms index hole 31, neck 32, and contact hole 33.

In a further embodiment of the invention, a second electrode layer (not shown) comprising an adhesive layer and glucose sensing layer would be attached to conductive substrate 12 as illustrated in FIG. 3. A contact area for a reference electrode for all of the strips within the array may be formed using a single area within conductive substrate 12. However, individual contacts must be made for working electrode 36 for all of the strips within the array. In the embodiment of this invention, index hole 31 is used to index the strip cartridge so that it can move a fresh strip to a test position. Neck 32 is punched in between 2 adjacent strips. The purpose of neck 32 is to facilitate the strip bending at the location of neck 32. In order for the strip to be expressed such that a user can apply blood, the strip is bent downward and neck 32 facilitates bending at a defined location. Contact hole 33 on conductive substrate 12 allows electrical contact to be made with a working electrode on an insulating substrate.

In a method of lancing in accordance with the present invention, a lance similar to the embodiments illustrated in FIGS. 1 through 3 is provided having a lancing element 22 with a sharpened tip 38, a separation element 24 having a separation tip 40 is positioned proximal to sharpened tip 38. In one embodiment of the invention the separation tip 40 may be positioned between approximately 0.005 inches and 0.020 inches proximal to sharpened tip 38. A method according to the present invention further includes the step of providing a connector connecting the proximal end of lancing element 22 to the proximal end of separation element 24 wherein the connector forms a fill channel 21 extending from the proximal end of lancing element 22 and the proximal end of separation element 24 to a working electrode 36 of sensor strip 100. The method further including the steps of inserting the lancing element into skin to form an incision, inserting the separation element 24 to further open the incision and maintaining the position of the lancing element 22 and the separation element 24 in the incision while blood or other bodily fluids are drawn into a gap 42 between the lancing element 22 and separation element 24. The method further comprising the step of drawing the bodily fluids from gap 42 into fill channel 21.

A lance 15 constructed in accordance with the present invention is beneficial due to the seamless transition between the tip section and the capillary section, and because the tip itself is a type of capillary. The unique construction of this design better insures that bodily fluids enter the fill channel 21 regardless of the height of the tip above or below the skin wound, or even if the tip lies horizontally offset from the wound, where the lance acts as a conduit for the bodily fluids.

A sensor strip 100 constructed according to the present invention is more easily by manufactured than a closed channel sensor strip. Such a strip may be manufactured by, for example, injection molding, embossing, or chemical etching, or even simple machining. While the capillary force of an open channel may be weaker than a comparable closed channel, the weakness can be overcome with the use of, for example, hydrophilic surface treatments or surfactant coatings including: Tween-80, a product of Sigma Chemical Co., St. Louis, Mo.; Aerosol OT a product of Cytec Industries, West Paterson, N.J.; JBR-515, a product of Jeneil Biosurfactant Company of Saukville, Wis.; and Niaproof a product of Sigma Chemical Co., St. Louis, Mo.

A sensor strip 100 constructed according to the present invention may have improved transfer properties because the invention described herein prevents the creation of a vacuum block in fill channel 21 that would prevent fluid from moving through the fill channel 21 and onto the measurement pad. With a closed channel capillary, the inlet must be positioned or designed to ensure that air is not prevented from freely entering the capillary during transfer into the measurement area. Thus, in a closed channel system, if the inlet is positioned too close to the wound or even inside it, flow may be disrupted or stopped. With the open channel of a sensor strip designed in accordance with the present invention, however, the inlet to the channel can be positioned arbitrarily close to the source of the blood.

Another advantage of a strip in accordance with the present invention including an open channel is that such a strip has the capacity to hold a larger volume of fluid than the minimum required to fill and initiate transfer into the measurement pad. One embodiment of the present invention the minimum volume required to fill the lance such that the column of fluid reaches the measurement pad is approximately 230 nL. However, lancing may produce quantities which are greater than 230 nL. Because of the open channel form in the present invention, the excess blood that is presented to the lance will continue to accumulate along the lance channel, forming a bulging drop of blood. This property is useful in that it clears away excess blood from the skin, leaving a cleaner lance wound.

Another advantage of the open channel design in accordance with the present invention is that a drop of fluid can be applied to the side of the lance rather than just at the tip of the lance (i.e. in a closed channel there is a distinct area where fluid must be presented to be drawn into the capillary). Manual application of blood might be required if the blood comes from a site that has been lanced separately. Thus, using a sensor strip designed in accordance with the present invention, provides the option of 'side' filling increases the user's options.

In one embodiment of the present invention, the stamped metal of conductive substrate 12 could also serve as a working or counter electrode. A unique aspect of the sheet metal design used in the present invention is the fact that it also allows the assembly to be constructed with first electrical contact 10 and second electrode contact 17 on the same side of the strip. This greatly simplifies the requirements for mating contacts on a meter because conductive substrate 12 comprises a solid conductor allowing electrical contact to be established from both the top and bottom side of conductive substrate 12, wherein the top side of conductive substrate 12 is on the same side as second electrical contact 17 and the bottom side of conductive substrate is on the same side as reference electrode 37.

On a conventionally constructed electrochemical strips using a facing electrode arrangement where both working and reference electrodes are printed or applied onto an insulating substrate, the electrical contacts must be positioned on opposites sides of the strip making the meter contacts more complex. If reference electrode 37 was printed or applied onto an insulating substrate, conductive substrate 12 would be insulated on the top side preventing electrical connection to be established from the top side. It could be possible to establish electrical connection from the top side if there was a partial removal of insulation from conductive substrate 12, however, this would add additional complexity to the manufacturing of the strip.

Finally, because sheet metal forming can be done as a progressive die stamping, in a strip designed in accordance with the present invention with individual lances chained together in series, it could be possible to construct an array of test sensors with a single, common reference thus requiring just one contact.

It will be recognized that equivalent structures may be substituted for the structured illustrated and described herein and that the described embodiment of the invention is not the only structure which may be employed to implement the claimed invention. In addition, it should be understood that every structure described above has a function and such structure can be referred to as a means for performing that function.

While preferred embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A lance comprising:
a substantially planar lancing element having a sharpened end point at a distal end thereof,
a single, substantially planar separation element having a separation tip, said separation tip positioned proximal to said sharpened endpoint;
a fill channel, said fill channel connecting a proximal end of said lancing element to a proximal end of said separation element wherein said lancing element is connected to said separation element only at said proximal end of said separation element;
said fill channel comprising:
a wall extending the length of said fill channel;
an opening extending the length of said fill channel;
said lancing element and said separation element forming a gap therebetween, said gap being wider at its proximal end than its distal end.

2. A lance according to claim 1 wherein said separation element is positioned at an angle to said lancing element.

3. A lance according to claim 1, wherein said lancing element, said separation element and said channel are formed from a single sheet of metal.

4. A lance according to claim 1, wherein at least a portion of said channel is treated with a hydrophilic surface coating.

5. A lance according to claim 1, wherein at least a portion of said lancing element and at least a portion of said separation element are coated with a hydrophilic surface coating.

6. A lance in accordance with claim 1, wherein a proximal end of said channel is integrated into a sensor strip.

7. A lance in accordance with claim 6, wherein said sensor strip is connected at a proximal end thereof to a plurality of additional sensor strips.

* * * * *